United States Patent [19]

Malabarba et al.

[11] Patent Number: 4,585,589
[45] Date of Patent: Apr. 29, 1986

[54] WATER-SOLUBLE ALKANOYLOXY AND ALKOXYCARBONYLOXY RIFAMPICIN DERIVATIVES, PROCESS FOR ITS PREPARATION, INTERMEDIATES, AND ITS PHARMACEUTICAL COMPOSITION AS ANTIBACTERIALS

[75] Inventors: Adriano Malabarba; Bruno Cavalleri, both of Milan; Pietro Ferrari, Paderno Dugnano, all of Italy

[73] Assignee: Gruppo Lepetit S.p.A., Italy

[21] Appl. No.: 626,358

[22] Filed: Jun. 29, 1984

[30] Foreign Application Priority Data

Jul. 4, 1983 [GB] United Kingdom ............... 8318072

[51] Int. Cl.$^4$ .............................................. C07D 498/08
[52] U.S. Cl. ............................... 260/239.3 P; 514/183
[58] Field of Search ................... 260/239.3 P; 514/183

[56] References Cited

U.S. PATENT DOCUMENTS

| | | | |
|---|---|---|---|
| 3,342,810 | 9/1967 | Maggi et al. | 260/239.3 P |
| 3,542,762 | 11/1970 | Gianantonio et al. | 260/239.3 P |
| 3,963,705 | 6/1976 | Marsili et al. | 260/239.3 P |
| 4,174,320 | 11/1979 | Bruzzese | 260/239.3 P |
| 4,188,321 | 2/1980 | Maggi et al. | 260/239.3 P |
| 4,298,692 | 11/1981 | Schupp et al. | 260/239.3 P |
| 4,411,896 | 10/1983 | Schupp et al. | 260/239.3 P |

OTHER PUBLICATIONS

Kim et al., Chem. Abst. 98-95561u (1983).
Greenaway et al., Chem. Abst. 99-63902k (1983).
Tan et al., Chem. Abst. 102-84467t (1985).
Malabarba et al., Chem. Abst. 103-6153u (1985).

*Primary Examiner*—Donald G. Daus
*Assistant Examiner*—Cecilia Shen
*Attorney, Agent, or Firm*—Stephen L. Nesbitt

[57] ABSTRACT

The present invention is directed to new water soluble rifampicin derivatives which are suitable for preparing aqueous solutions for oral or parenteral administration. The new derivatives of the invention are 4 and/or 8 alkanoyl or alkanoyloxyalkyl esters of rifampicin and possess essentially the same antibacterial activity of this widely known antibiotic substance.

9 Claims, No Drawings

WATER-SOLUBLE ALKANOYLOXY AND ALKOXYCARBONYLOXY RIFAMPICIN DERIVATIVES, PROCESS FOR ITS PREPARATION, INTERMEDIATES, AND ITS PHARMACEUTICAL COMPOSITION AS ANTIBACTERIALS

Rifampicin, i.e. 3-[[(4-methyl-1-piperazinyl)imino]-methyl]rifamycin, is a widely known antibacterial agent which shows a broad antibacterial spectrum and is used world-wide as the first choice agent in the treatment of tuberculosis and in many countries also for the treatment of other infectious diseases.

The dosage forms containing rifampicin available on the market are limited to those designed for oral administration (capsules and syrups) (see Martindale, "The Extrapharmacopeia", 28th Edition, The Pharmacological Press—London (1982), p.1582) and in some countries also to phlebo formulations for i.v. infusions (see G. Perna, F. Natale, "Intravenous use of rifampicin in tuberculous diseases", Clin. Ter. 90, 63–73 (1979). However, the phlebo formulations have been employed for clinical use only for the treatment of severely ill patients and the intravenous treatment is changed to the oral administration as soon as possible to avoid the possible development of undesired side-effects connected with this route of administration.

No intramuscular preparation of this drug is available at present. The solubility of rifampicin in various aqueous media, at a pH compatible with local tolerability requirements (3.5<pH<7.5), is in fact lower than 20 mg/ml (see K. Florey, Analytical Profiles of Drug Substances, Vol. 5, p. 489, Academic Press, New York, 1976) either in the presence or absence of excipients and/or co-solvents, while the solubility required for an intramuscular formulation should be about 100 mg/ml. The possibility of intramuscularly administering a drug however has many advantages as in fact this would allow delivery even when oral therapy is not feasible (e.g. when patients have a gastrointestinal in tolerance, or in pediatrics) and would give more rapid and also more reliable (because not affected by the different absorption by the gastrointestinal tract) blood levels of the administered drug. The importance of these advantages in the present case could be better weighed considering that rifampicin is a life-saving drug.

We have now discovered that a bioreversible chemical modification of the rifampicin molecule, and more particularly the replacement of the 8-hydroxy or the 8- and 4-hydroxy groups of the rifampicin skeleton with one or two lower alkanoyloxy or lower alkoxy-carbonyloxy groups, leads to new rifampicin derivatives that possess high water solubility. These derivatives, owing to the presence in animal tissues (mainly in blood and liver) of aspecific acyl esterases able to cleave various ester bonds, easily regenerate rifampicin in vivo.

The water solubility of the new rifampicin derivatives makes the new compounds particularly suitable for a formulation for intramuscular use. Moreover, although aqueous formulations of the new rifampicin derivatives of formula I are particularly suitable for intramuscular administration, they could be employed also for other administration routes when a water soluble rifampicin is required. As an example, aqueous formulations of the new compounds could be utilized advantageously for pediatric droplets in case of oral administration, or for intraarticular administration in the treatment of rheumatoid arthritis and allied pathologic conditions. It was recently reported in fact that some rifamycin salts proved to be very useful in this therapy (I. Caruso et al, Annals of Rheumatic Diseases, 1982, vol. 41, pp. 232–236).

Accordingly, the present invention provides for the new rifampicin derivatives, the process for their manufacture as well as the intermediates therein and the pharmaceutical formulations containing the new compounds, particularly the liquid pharmaceutical formulations suitable for intramuscular, intraarticular and oral administration.

The novel rifampicin derivatives of the present invention have the following formula

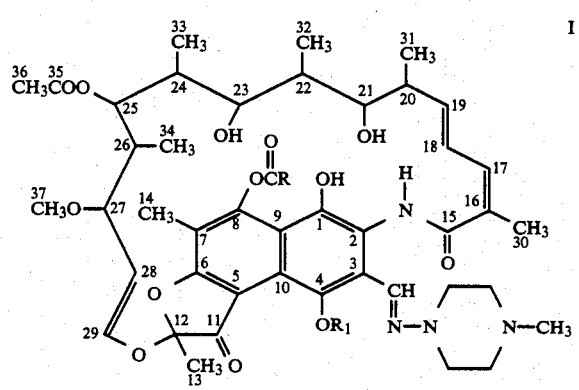

wherein R stands for a $(C_1-C_3)$alkyl or $(C_1-C_3)$alkoxy group and $R_1$ may represent hydrogen or an aliphatic acyl radical containing 2 to 4 carbon atoms.

As used herein, the terms "$(C_1-C_3)$alkyl" and "$(C_1-C_3)$alkoxy" designate linear or branched alkyl and alkoxy radicals containing from 1 to 3 carbon atoms i.e. methyl, ethyl, propyl, and isopropyl, and methoxy, ethoxy, propoxy and isopropoxy respectively, while the term "aliphatic acyl radical containing 2 to 4 carbon atoms" is intended to indicate essentially acetyl, propionyl, butyryl, and isobutyryl radicals.

A preferred group of compounds of the invention comprises those compounds of formula I wherein R is methyl, ethyl or ethoxy and $R_1$ is hydrogen or acetyl.

A most preferred group of compounds of the invention comprises those compounds of formula I wherein R is methyl and $R_1$ is hydrogen or acetyl.

The compounds of the present invention can not be prepared in acceptable yields and free from undesired by-products through direct acylation of rifampicin and all the experiments carried out changing the acylating agents and the reaction conditions failed to give the desired results. A new synthetic approach to the preparation of these compounds had to be studied which led the inventors to set up the following process which is summarized in Scheme I below (wherein the symbol Me represents $CH_3$—, i.e. a methyl group):

SCHEME I

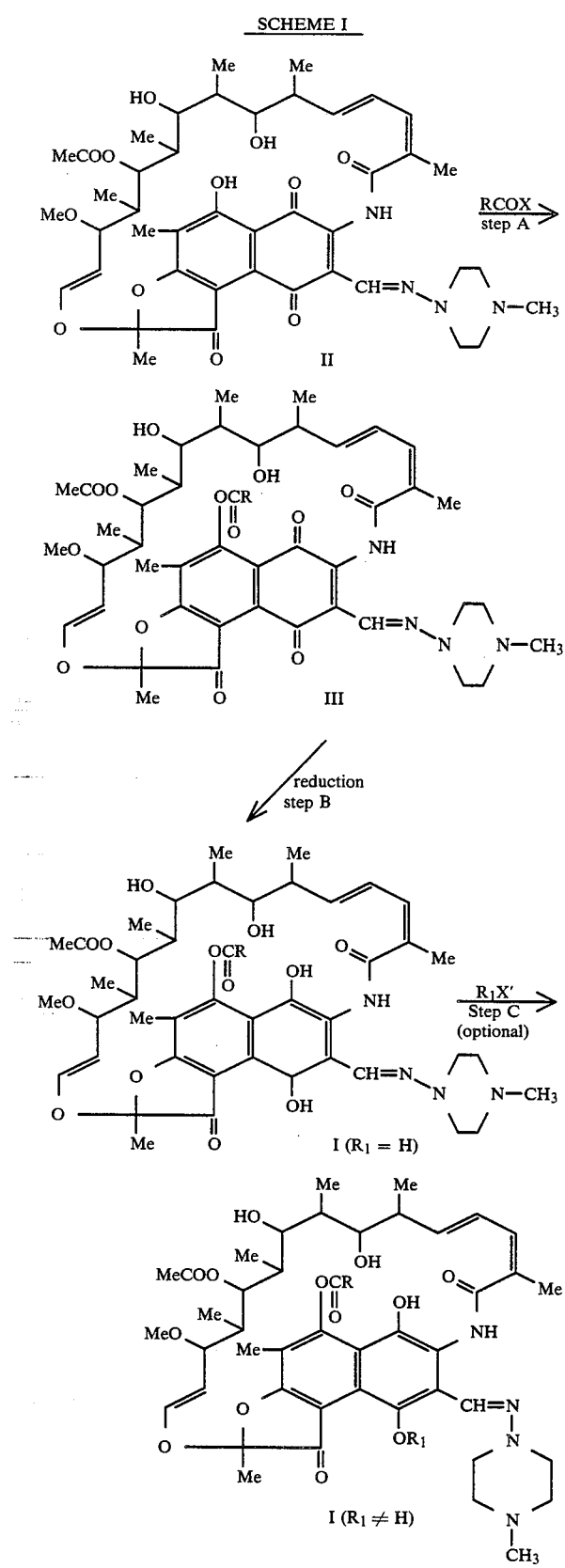

In particular, the compounds of the present invention are prepared starting from the quinone (oxidized form) of rifampicin (the compound of formula II) which is reacted, according to step (A) above, with a suitably selected acyl halide of formula RCOX wherein R is as defined before and X stands for chlorine or bromine. The molar proportion between the two reactants is not a critical parameter of the reaction as good results are obtained also when the two reaction partners are employed in equimolar amounts. However, a slight excess of the acyl halide over the rifampicin substrate (about 15-25% molar excess) is preferred.

This first step of the reaction is conveniently carried out in a polar or not polar aprotic organic solvent which does not negatively interfere with the reaction course. Examples of such a solvent are tetrahydrofuran, dioxane, methylene chloride, chloroform, carbon tetrachloride and like solvents.

A hydrogen halide acceptor is required to combine with the hydrogen halide which forms during the reaction. To this purpose, a tertiary organic nitrogen base, at least in equimolar proportion to the acyl halide reactant, is generally employed. Tri-(lower alkyl)amines, e.g. triethylamine, pyridine, picolines, collidines and the like can suitably be employed as hydrogen halide acceptors. When pyridine, picolines or collidines are employed, they can be used in high excess and act therefore also as the reaction solvent.

This first step of the reaction may be run at a temperature between −25° C. and room temperature, but preferably between −20° C. and +10° C. and most preferably between −5° C. and 5° C.

Generally the reaction is complete in a few hours; anyway, the course of the reaction can easily be monitored by checking the disappearance of the starting compound of formula II by means of thin layer chromatography.

Once this first step is complete, the intermediate compounds of formula III can be recovered from the reaction mixture by conventional techniques, which involve separation of the quaternary ammonium salt by filtration, concentration of the filtrate to a small volume and precipitation of the raw product of formula III by the addition of an organic solvent wherein the acylated intermediate III is much less soluble than the starting quinone II. If desired, the obtained intermediate can be further purified by crystallization from a suitable crystallization solvent.

According to the second step of the reaction pathway, step (B) the obtained 8-acyl quinone intermediate of formula III is reduced to the corresponding hydroquinone form, thus yielding the compounds of formula I wherein R is as desired and $R_1$ is hydrogen. Reduction of the quinone to the hydroquinone is accomplished by means of ascorbic acid which is known in the rifamycin chemistry to be capable of carrying out said reduction without affecting the other groups of the rifamycin molecule. The reduction reaction which takes a few minutes to be complete, is conveniently carried out at room temperature. The reaction is generally carried out in the presence of water and a suitable organic solvent, miscible or only partially miscible with water, which would not be affected by the presence of the mild reducing agent. At the end of the reaction, if a homogeneous phase is present, a polar organic solvent immiscible with water is added to give a two phase system, then the aqueous phase is separated and the obtained compound of formula I is recovered by concentrating it to a small volume and precipitating the end product therefrom by the addition of a non-solvent; the above procedure can then be repeated until a pure product is obtained.

Finally, if a compound of formula I is desired wherein $R_1$ is different from hydrogen, it can be obtained from the corresponding compound I wherein $R_1$ is hydrogen obtained as described above, by treatment with a suitable acyl halide of the formula $R_1X'$ wherein $R_1$ is an aliphatic acyl of 2 to 4 carbon atoms and $X'$ may represent chlorine or bromine.

The reaction conditions suitable for the step (C) acylation correspond more or less to those described above for step (A). Also in this case the reaction requires the use of a hydrogen halide acceptor and of a polar aprotic organic solvent which does not interfere unfavorably with the reaction course. The end product is then recovered by conventional techniques and purified by crystallization from a suitable crystallization solvent.

The following examples will further illustrate some specific compounds of the invention and the method of manufacturing the novel compounds but in no way they should be interpreted as a limitation to the scope of the invention.

EXAMPLE 1

1,4-dideoxy-1,4-dihydro-3-[[(4-methyl-1-piperazinyl)imino]methyl]-1,4-dioxorifamycin 8-acetate Triethylamine (3.5 ml, about 25 mmole) is added at 0° C. with stirring to a solution of 1,4-dideoxy-1,4-dihydro-3-[[(4-methyl-1-piperazinyl)imino]methyl]-1,4-dioxorifamycin (16.4 g, 20 mmole) in anhydrous tetrahydrofuran (500 ml). Afterwards a solution of acetyl chloride (1.78 ml, 25 mmole) in anhydrous tetrahydrofuran (150 ml) is added dropwise at −5° C. with stirring. The reaction mixture is then allowed to stand for 2 hours at −50° C. and for further 3 hours at room temperature. The resulting suspension is filtered and the filtrate is concentrated to a small volume under vacuum at 35° C. Upon addition of n-hexane, a solid separates which is collected by filtration and dissolved in a small amount of ethyl acetate. A mixture of ether and n-hexane ¼ (v/v) is then added to the ethyl acetate solution and the solid which separates is collected by filtration, washed with n-hexane and recrystallized from ethyl acetate yielding 15.5 g of the compound of the title (90% yield). The I.R., and N.M.R. spectra which are reported in following Tables I and III, confirm the assigned structure.

EXAMPLES 2 and 3

By following substantially the same procedure of Example 1, but using the proper acyl chloride, the following compounds are prepared:

(2) 1,4-dideoxy-1,4-dihydro-3-[[(4-methyl-1-piperazinyl)imino]methyl]-1,4-dioxorifamycin 8-propanoate
(Yield: 82%)

(3) 1,4-dideoxy-1,4-dihydro-3-[[(4-methyl-1-piperazinyl)imino]methyl]-1,4-dioxorifamycin 8-ethylcarbonate
(Yield: 65%)

The physico-chemical data for the compounds of examples 2 and 3 which are reported in following Tables I, II, and III, confirmed the assigned structures.

TABLE I

I.R. spectra

I.R. spectral data ($cm^{-1}$), obtained in $CDCl_3$ solution, of the compounds of Examples 1, 2 and 3 in comparison with the starting rifampicin-quinone of formula II are listed in the following table

TABLE I

| Compound | R | ansa chain from $C_{21}$ to $C_{25}$ | | | dienamide moiety | | |
|---|---|---|---|---|---|---|---|
| | | $\nu$OH | $\nu C_{35}=O$ | $\nu C_{35}-O-C_{25}$ | $\nu$NH | amide I | amide II |
| of formula II | | 3470 | 1710 | 1260 | 3200 | 1685 | 1455 |
| of Example 1 | —$CH_3$ | 3480 | 1710 | 1260 | 3200 | 1695 | 1455 |
| of Example 2 | —$CH_2CH_3$ | 3480 | 1710 | 1260 | 3200 | 1695 | 1455 |
| of Example 3 | —$OCH_2CH_3$ | 3480 | 1710 | 1260 | 3200 | 1690 | 1455 |

| Compound | $\nu$OH | $C_8$—acyl | | furanone chromophore | | | | $\delta$OH |
|---|---|---|---|---|---|---|---|---|
| | | $\nu C=C$ | $\nu C-O-C$ | $\nu C=O$ | $\nu C_4=O$ | $\nu C_1=O$ | $\nu C=C$ | |
| of formula II | 3000–2500 | — | — | 1730 | 1665 | 1630 | 1590, 1540 | 1415 |
| of Example 1 | — | 1775 | 1190 | 1735 | 1665 | 1665 | 1585, 1540 | — |
| of Example 2 | — | 1770 | 1120 | 1740 | 1670 | 1670 | 1585, 1540 | — |
| of Example 3 | — | 1765 | 1240 | 1740 | 1670 | 1670 | 1590, 1540 | — |

I.R. spectra were recorded with a Perkin Elmer Model 580 spectrophotometer

TABLE II

UV-VIS spectra data of the compounds of Examples 2 and 3 in aqueous buffer pH 7.38 in comparison with that of the starting rifampicin-quinone of formula II are reported in the following Table

TABLE II

| Compound | R | $\lambda$ (nm), $E^{1\%}_{1cm}$ | | | | |
|---|---|---|---|---|---|---|
| of formula II | | 220 (382) | 260 (341) | 332 (343) | 385 (sh) | 530 (71) |
| of Example 2 | —$CH_2CH_3$ | 220 (307) | 265 (314) | 332 (281) | 445 (80) | 550 (br) |
| of Example 3 | —O—$CH_2CH_3$ | 220 (312) | 265 (309) | 332 (261) | 440 (79) | 550 (br) | br = broad
sh = shoulder

UV-VIS spectra were obtained with a Perkin-Elmer model 320 spectrophotometer.

TABLE III

$^1$H-NMR spectra

Some $^1$H-NMR data in CDCl$_3$ solution for the compounds of Examples 1, 2 and 3 in comparison with the starting rifampicin-quinone of formula II are reported in the following Table. No significant differences in chemical shift are shown by the other protons

TABLE III

| Compound R Proton | of formula II — | | | of Example 1 —CH$_3$ | | | of Example 2 —CH$_2$CH$_3$ | | | of Example 3 —OCH$_2$CH$_3$ | | |
|---|---|---|---|---|---|---|---|---|---|---|---|---|
| | Mult. | δ | J | Mult. | δ | J | Mult | δ | J | Mult. | δ | J |
| R | b | 13.2 | — | s | 2.50 | — | m | 2.81 | — | m | 4.43 | — |
| | | | | | | | t | 1.34 | — | t | 1.43 | 7 |
| NHCO | bs | 10.52 | — | bs | 10.87 | — | bs | 10.86 | — | bs | 10.72 | — |
| H-17 | d | 6.40 | 11 | d | 6.28 | 11 | d | 6.25 | 11 | d | 6.27 | 11 |
| H-18 | dd | 6.84 | 16 | dd | 6.63 | 16 | dd | 6.60 | 16 | dd | 6.66 | 16 |
| H-19 | dd | 6.11 | 5.5 | dd | 5.88 | 5 | dd | 5.87 | 5 | dd | 5.90 | 5 |
| H-26 | ddq | 1.42 | 1 | ddq | 1.37 | 1.5 | ddq | 1.36 | 1.5 | ddq | 1.37 | 1.5 |
| H-28 | dd | 5.07 | 12.5 | dd | 5.16 | 12 | dd | 5.14 | 12 | dd | 5.13 | 12 | b = broad
bs = broad singlet
s = singlet
d = doublet
dd = doublet of doublets
ddq = doublet of doublets of quartets
m = multiplet
t = triplet
$^1$H-NMR spectra were recorded at 270 MHz with a Bruker WH-270 cryospectrometer with TMS as internal reference (δ = 0)
(δ = ppm, J = Hz)

EXAMPLE 4

3-[[(4-methyl-1-piperazinyl)imino]methyl]rifamycin 8-acetate

A solution of L-(+)-ascorbic acid (3.52 g, 20 mmole) in water (800 ml) is added at room temperature with stirring to a solution of the compound of example 1 (8.6 g, 10 mmole) in ethyl acetate (800 ml). The reaction mixture is kept at room temperature for 30 minutes, afterwards the aqueous layer is separated and the organic phase is reextracted with water (800 ml). The aqueous layers are combined and washed with ethyl acetate (400 ml), then treated with 0.5 M phosphate buffer pH 7.38 up to pH 7.2 and extracted with methylene chloride (3×500 ml). The methylene chloride layers are pooled, washed with water (1000 ml), dried over CaCl$_2$ and concentrated to a small volume. Upon addition of petroleum ether a solid separates which is collected by filtration and dissolved in ethyl acetate (260 ml). Ether (750 ml) is then added to the ethyl acetate solution and the solid which precipitates is filtered off. The remaining solution is allowed to stand at room temperature for 3 days and the red crystals which separate are recovered by filtration yielding 3-[[(4-methyl-1-piperazinyl)imino]methyl]rifamycin 8-acetate (7.35 g, 85%) as a pure compound. The I.R., UV-VIS, and $^1$H-NMR data, which are reported in following tables IV, V, and VI, confirm the assigned structure.

EXAMPLE 5

3-[[(4-methyl-1-piperazinyl)imino]methyl]rifamycin 8-pro- panoate

The compound of the title is prepared by following substantially the same procedure as in the foregoing Example but starting from the compound of Example 2. Yield: 62%.

The IR, UV-VIS, and $^1$H-NMR data for the obtained compound are reported in Tables IV, V, and VI.

EXAMPLE 6

3-[[(4-methyl-1-piperazinyl)imino]methyl]rifamycin 8-ethylcarbonate

L-(+)-ascorbic acid (0.7 g, 4 mmole) is added portionwise at room temperature to a stirred solution of the compound of example 3 (3.57 g, 4 mmole) in methanol (175 ml). The reaction mixture is kept at room temperature for 30 minutes, then concentrated to half volume. Upon cooling, a solid separates which is collected by filtration and dissolved in methylene chloride (50 ml). Methanol (80 ml) is added to the obtained solution and methylene chloride is evaporated under vacuum at 20° C. On standing overnight at room temperature, the compound of the title separates as orange crystals which are collected and washed with ether, then dried in vacuo at room temperature. Yield: 56%.

Physico-chemical data of the compound of the title are listed in Tables IV, V, and VI.

EXAMPLE 7

3-[[(4-methyl-1-piperazinyl))imino]methyl]rifamycin 4,8-diacetate

Triethylamine (0.28 ml, about 2 mmole) is added at 0° C. to a stirred solution of the compound of example 4 (1.73 g, 2 mmole) in methylene chloride (170 ml). Afterwards, a solution of acetyl chloride (0.14 ml, 2 mmole) in anhydrous tetrahydrofuran (1.5 ml) is added dropwise at −20° C. with stirring. The reaction mixture is kept 1 hour at 0° C. and 3 hours at room temperature, then it is extracted with water (200 ml). The organic layer is separated, dried over CaCl$_2$ and concentrated to a small volume. Upon addition of n-hexane a solid separates which is collected and crystallized from a mixture of ethyl acetate/ether 1/1 (v/v) giving the compound of the title (1.29 g, 71%) as orange crystals. Physico-chemical data of the compound of the title, which confirm the assigned structure, are reported in the following Tables:

TABLE IV

IR spectra

IR spectral data (cm$^{-1}$), obtained in CDCl$_3$ solution, of the compounds of Examples 4, 5, 6 and 7 in comparison with rifampicin, are reported hereinbelow:

TABLE IV

| Compound | R | $R_1$ | ansa chain from $C_{21}$ to $C_{25}$ | | | dienamide moiety | | | chromophore | | | furanone | |
|---|---|---|---|---|---|---|---|---|---|---|---|---|---|
| | | | | | | | amide I (mainly $\nu C=O$) | amide II (mainly $\delta NH$) | | $C_4$ and/or $C_8$—acyl | | | |
| | | | $\nu OH$ | $\nu C_{35}=O$ | $\nu C_{35}-O-C_{25}$ | $\nu NH$ | | | $\nu OH$ | $\nu C=O$ | $\nu C-O-C$ | $\nu C=O$ | $\nu C=C$ |
| rifampicin | | | 3480 | 1710 | 1260 | 3300–2300 | 1625 | 1540 | 3300–2300 | — | — | 1645 | 1565 |
| of Example 4 | —CH$_3$ | H | 3480 | 1710 | 1250 | 3300–2300 | 1660 | 1530 | 3300–2300 | 1765 | 1190 | 1650 | 1560 |
| of Example 5 | CH$_2$CH$_3$ | H | 3480 | 1715 | 1250 | 3300–2300 | 1660 | 1530 | 3300–2300 | 1765 | 1120 | 1650 | 1560 |
| of Example 6 | OCH$_2$CH$_3$ | H | 3480 | 1715 | 1255 | 3300–2300 | 1665 | 1530 | 3300–2300 | 1765 | 1245 | 1650 | 1565 |
| of Example 7 | CH$_3$ | COCH$_3$ | 3490 | 1715 | 1255 | 3300–2500 | 1665 | 1525 | 3300–2500 | 1765, 1775 | 1190 | 1730 | 1570 |

TABLE V

UV-VIS spectra of compounds of Examples 4, 5 and 6 were recorded in aqueous phosphate buffer solution at pH 7.38 in comparison with rifampicin. Spectral data ($\lambda_{max}$ and $E_{1\ cm}^{1\%}$) are listed in the following Table:

TABLE V

| Compound | R | $R_1$ | $\lambda$ (nm), $E_{1cm}^{1\%}$ | | | | |
|---|---|---|---|---|---|---|---|
| rifampicin | | | 237 (403) | 255 (380) | 334 (328) | | 475 (187) |
| of Ex. 4 | CH$_3$ | H | 236 (404) | 260 (sh) | 328 (286) | 425 (sh) | 445 (221) |
| of Ex. 5 | CH$_2$CH$_3$ | H | 236 (366) | 260 (sh) | 328 (269) | 425 (sh) | 445 (229) |
| of Ex. 6 | OCH$_2$CH$_3$ | H | 236 (361) | 260 (sh) | 330 (268) | 425 (sh) | 445 (218) | sh = shoulder

TABLE VI $^1$H-NMR spectra

A few significant $^1$H-NMR data for the compounds of Examples 4, 5, 6, and 7 in comparison with rifampicin are reported in the following Table. Rifampicin and the compounds of Examples 4, 6, and 7 were dissolved in CDCl$_3$ while the compound of Example 5 was dissolved in CD$_3$OD acid and 10% propylene glycol (solution B) and the pH of the resulting solutions was recorded.

The results obtained show that while rifampicin solubility in either solution is less than 50 mg/ml with a pH of about 3.5–3.6, the solubility of the compounds of the present invention and the pH of the obtained solutions are much higher. As an example, the compound of example 4 has a solubility of 100 mg/ml with a pH of 4.0 in solution A and of 150 mg/ml with a pH of 4.2 in solution B, while the compound of Example 7 has a solubility of more than 300 mg/ml in solution A with a pH of 4.5.

The good in vivo rifampicin release characteristics of the compounds of the present invention have been ascertained by means of blood level studies in mice which

TABLE VI

| | Rifampicin | | | of Example 4 | | | of Example 5 R,R$_1$ | | | of Example 6 | | | of Example 7 | | |
|---|---|---|---|---|---|---|---|---|---|---|---|---|---|---|---|
| | | | | R=CH$_3$ R'=H | | | R=CH$_2$CH$_3$ R'=H | | | R=OCH$_2$CH$_3$ R'=H | | | R=CH$_3$ R'=COCH$_3$ | | |
| Proton | Mult. | δ | J | Mult. | δ | J | Mult. | δ | J | Mult. | δ | J | Mult. | δ | J |
| OH—1 | b | 12.5 | — | s | 11.43 | — | — | — | — | s | 11.38 | — | s | 11.60 | — |
| OH—4 | s | 13.11 | — | s | 1293 | — | — | — | — | s | 12.93 | — | — | — | — |
| OH—8 | b | 12.5 | — | — | — | — | — | — | — | — | — | — | — | — | — |
| R | — | — | — | s | 2.47 | — | t | 1.22 | — | t | 1.44 | 7 | s | 2.47 | — |
| | | | | | | | q | 2.67 | — | q | 4.40 | — | | | |
| R' | — | — | — | — | — | — | — | — | — | — | — | — | s | 2.23 | — |
| NHCO | s | 12.0 | — | s | 11.15 | — | — | — | — | s | 11.13 | — | s | 11.29 | — |
| H—17 | d | 6.42 | 10 | d | 6.38 | 10.5 | d | 6.42 | 11 | d | 6.37 | 10 | d | 6.47 | 10 |
| H—18 | dd | 6.60 | 15 | dd | 6.62 | 15 | dd | 7.22 | 16 | dd | 6.63 | 15 | dd | 6.82 | 15.5 |
| H—19 | dd | 5.92 | 7 | dd | 5.92 | 5 | dd | 6.13 | 6.5 | dd | 5.90 | 4 | dd | 5.90 | 5 |
| OH—21 | d | 3.43 | 1 | b | 3.4 | — | — | — | — | s | 3.36 | — | b | 3.73 | — |
| OH—23 | d | 3.60 | 2 | b | 3.4 | — | — | — | — | d | 3.57 | 4 | b | 3.49 | — |
| H—26 | ddq | 1.37 | 1.5 | ddq | 1.28 | 1 | ddq | 1.29 | 1 | ddq | 1.29 | 1.5 | ddq | 1.58 | 2 |

The compounds of the present invention show a marked solubility in water as well as in mixtures of water with other pharmaceutically acceptable solvents miscible with water. In particular, the solubility of the compounds of the present invention in comparison with rifampicin was assayed in water containing 2% ascorbic acid (solution A) and in water containing 2% ascorbic show that single subcutaneous doses of 20 mg/kg of the compounds of the present invention in mice produce blood levels (as measured by serum concentration of rifampicin released from the esters) which are only slightly lower than those obtained by administering rifampicin directly, and provide for the maximum level of rifampicin after about 1 hour from the administration. As expected, this slight delay in hydrolysis in vivo reflects in a median effective dose (ED$_{50}$) for the compounds of formula I somewhat higher than for rifampicin. In particular the antibacterial activity of the compounds of the present invention was tested in mice infected with *Staphylococcus aureus* Tour. The ED$_{50}$s of the compounds of Examples 4, 5, 6, and 7, when administered subcutaneously, are reported in the following Table VII

TABLE VII

| Compound of Example No. | ED$_{50}$ (mg/kg) s.c. against *S. aureus* Tour | |
|---|---|---|
| 4 | 0.35 | (0.31–0.40) |
| 5 | 1.2 | (1.0–1.5) |
| 6 | 0.76 | (0.68–0.85) |
| 7 | 1.5 | (1.4–1.7) |

The pharmaceutical liquid preparations for oral, intramuscular or intraarticular use containing a compound of formula I as the active ingredient, will contain it in amounts which are consistent with a suitable dosage and with the solubility properties of the particular compound employed.

Particularly desirable compositions however are those prepared in the form of dosage units, i.e. measured volumes of liquid compositions, containing from about 50 to about 1000 mg and preferably from about 150 to about 500 mg of a compound of formula I per unit. The solvents which may be employed for the liquid preparations of the present invention are generally water or mixtures of water and polyhydric aliphatic alcohols such as ethyl alcohol, polyethylene glycol of the liquid series and propylene glycol. Besides the antibacterially active ingredient, additional substances may be added to the composition to improve or safeguard the quality of the product. In particular, the pharmaceutical liquid preparations of the present invention may contain antioxidants, typically ascorbic acid to prevent formation of the oxidized quinonic form, preservatives, dispersing or wetting agents, buffering agents and other suitable additives known to be useful in the preparation of the particular compositions desired. Furthermore, if desired, the liquid compositions of the present invention may contain also other active ingredients. Other active ingredients can include, for example, other water-soluble antibacterial agents which, when associated to rifampicin, may give rise to a synergistic effect, and, when preparations for intramuscular or intraarticular use are desired, local anesthetics and analgesic agents. The compositions can be prepared by techniques known in the art for the preparation of solutions for oral use or sterile injectable compositions (see for instance Remington's Pharmaceutical Sciences, 13th Ed., Mack Publishing Co. Easton, Penna.).

They may be in the form of solutions ready for use or as dry soluble products ready to be combined with a suitable aqueous vehicle just prior to use. As an example, suitable dosage units for extemporaneous intramuscular use may be prepared by dissolving the content of a vial of lyophilized material containing 300 mg of the compound of Example 4 in 3 ml of sterile water for injection containing 2% ascorbic acid or the content of a lyophilized vial consisting of 500 mg of the compound of Example 5 in 4 ml of sterile water for injection containing 15% propylene glycol and 2% ascorbic acid.

Other dosage units for extemporaneous intramuscular use may be prepared by dissolving the content of a vial of lyophilized or powdered active principle of the invention (e.g. 315 mg of the compound of example 4 or 320 mg of the compound of example 5 in admixture with 10% ascorbic acid) in sterile water for injections (e.g. 3.5 ml for 315 mg of the compound of example 4 or 4 ml for 320 mg of the compound of example 5) or in sterile water for injection plus 10% polypropylene glycol (e.g. 3 ml for 315 mg of the compound of example 4 or 3.5 ml for 320 mg of the comopund of example 5).

We claim:

1. A compound of the formula

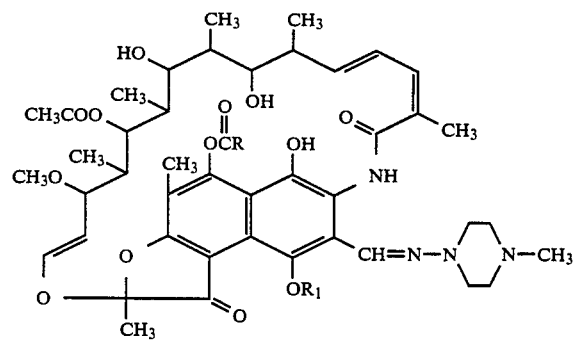

wherein R is a (C$_1$–C$_3$)alkyl or (C$_1$–C$_3$)alkoxy group; and R$_1$ is a hydrogen or a (C$_2$–C$_4$)alkanoyl group.

2. A compound as in claim 1 wherein R is methyl, ethyl or ethoxy and R$_1$ is hydrogen or acetyl.

3. A compound as in claim 1 wherein R is methyl or ethyl and R$_1$ is hydrogen.

4. A process for preparing a compound of formula I

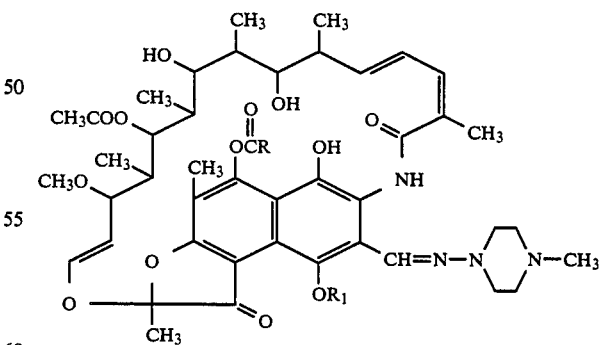

wherein R is a (C$_1$–C$_3$)alkyl or (C$_1$–C$_3$)alkoxy group; and R$_1$ is a hydrogen or a (C$_2$–C$_4$)alkanoyl group; which comprises reacting 1,4-dideoxy-1,4-dihydro-3[[(4-methyl-1-piperazinyl)imino]-methyl]-1,4-dioxorifampycin of formula II

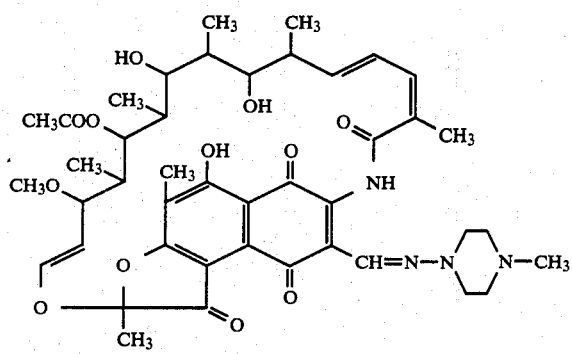

with a compound of formula RCOX wherein R is as defined above and X strands for chlorine or bromine, in the presence of a hydrogen halide acceptor and reducing the obtained intermediate of formula III

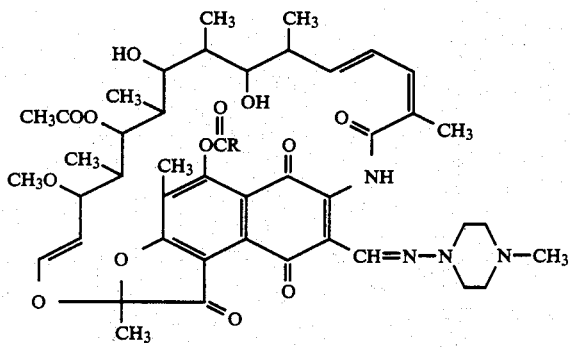

wherein R is a defined above, with ascorbic acid, acylating the corresponding compound thus obtained, through reaction with a compound of formula $R_1X'$ wherein $R_1$ is an alkanoyl acyl of from 2 to 4 carbon atoms and $X'$ is chlorine or bromine in the presence of a hydrogen halide acceptor.

5. An intermediate compound of formula

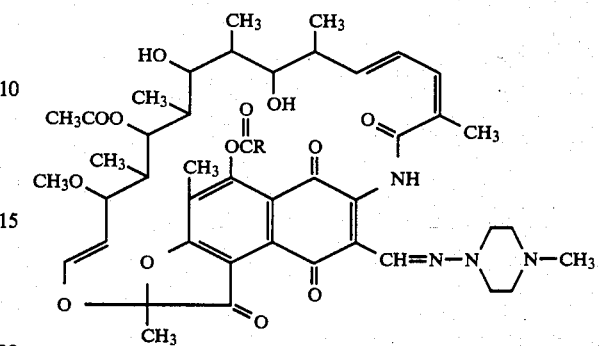

wherein R is a $(C_1-C_3)$alkyl or $(C_1-C_3)$alkoxy group.

6. A pharamceutical composition suitable for intramuscular administration which contains a compound of claim 1 as the active ingredient.

7. A liquid pharmaceutical composition containing a compound of claim 1 as the active ingredient and water of mixtures of water and polyhydric aliphatic alcohols as the pharmaceutically acceptable solvents.

8. A liquid pharmaceutical composition containing a compound of claim 1 as the active ingredient and water of mixtures of water and polyhydric aliphatic alcohols as the pharmaceutically acceptable solvents which further contains an antioxidant agent.

9. A pharmaceutical composition as in claim 8 wherein the antioxidant agent is ascorbic acid.

* * * * *

UNITED STATES PATENT AND TRADEMARK OFFICE
CERTIFICATE OF CORRECTION

PATENT NO. : 4,585,589
DATED : April 29, 1986
INVENTOR(S) : Adriano Malabarba et al.

It is certified that error appears in the above-identified patent and that said Letters Patent is hereby corrected as shown below:

At columns 9-10, Table VI, the term "Compound R,R₁" appears in the wrong location in the headings where it is centered above and below the term "of Example 5" and should appear in column 1 as follows:

TABLE VI

| Compound | Rifampicin | of Example 4 | of Example 5 | of Example 6 | of Example 7 |
|---|---|---|---|---|---|
| $R, R_1$ | | $R = CH_3\ R' = H$ | $R = CH_2CH_3\ R' = H$ | $R = OCH_2CH_3\ R' = H$ | $R = CH_3\ R' = COCH_3$ |

At columns 9-10, Table VI, in the column under Example 4, line 2, the patent reads "1293" and should read --12.93--

At column 14, line 5, claim 5, the patent reads "compound of formula" and should read --compound of formula III--

Signed and Sealed this

Eighth Day of January, 1991

Attest:

HARRY F. MANBECK, JR.

*Attesting Officer*          *Commissioner of Patents and Trademarks*